United States Patent
Sakamoto et al.

(10) Patent No.: US 8,859,809 B2
(45) Date of Patent: Oct. 14, 2014

(54) DEVICE AND PROCESS FOR CRYSTALLIZING (METH)ACRYLIC ACID

(75) Inventors: Kazuhiko Sakamoto, Himeji (JP); Koji Ueno, Himeji (JP); Yoshitake Ishii, Himeji (JP); Masatsugu Kitaura, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 275 days.

(21) Appl. No.: 13/381,449

(22) PCT Filed: Jun. 24, 2010

(86) PCT No.: PCT/JP2010/060755
§ 371 (c)(1),
(2), (4) Date: Dec. 29, 2011

(87) PCT Pub. No.: WO2011/001894
PCT Pub. Date: Jan. 6, 2011

(65) Prior Publication Data
US 2012/0108847 A1 May 3, 2012

(30) Foreign Application Priority Data
Jul. 3, 2009 (JP) .................................. 2009-158971

(51) Int. Cl.
*C07C 51/42* (2006.01)
*B01D 9/00* (2006.01)
*C07C 51/43* (2006.01)

(52) U.S. Cl.
CPC .............. *B01D 9/0013* (2013.01); *C07C 51/43* (2013.01)
USPC ........................................................ 562/600

(58) Field of Classification Search
CPC combination set(s) only.
See application file for complete search history.

(56) References Cited

U.S. PATENT DOCUMENTS

| 5,504,247 A * | 4/1996 | Saxer et al. ................... 562/600 |
| 7,183,428 B2 | 2/2007 | Ueno et al. |
| 2004/0249199 A1 | 12/2004 | Ueno et al. |
| 2008/0021238 A1 | 1/2008 | Yamagishi et al. |

FOREIGN PATENT DOCUMENTS

| JP | 7-48311 | 2/1995 |
| JP | 2005-15478 | 1/2005 |
| JP | 2005-336142 | 12/2005 |

OTHER PUBLICATIONS

First Notification of Office Action issued Aug. 12, 2013 in corresponding Chinese Application No. 201080027824.8 (with English translation).
International Search Report issued Sep. 14, 2010 in corresponding International Application No. PCT/JP2010/060755.
Japanese Office Action dated May 27, 2014 issued in corresponding Japanese Application No. 2011-520888 (with English translation).

* cited by examiner

*Primary Examiner* — Karl J Puttlitz
(74) *Attorney, Agent, or Firm* — Wenderoth, Lind & Ponack, L.L.P.

(57) ABSTRACT

A crystallization device and a crystallization process are provided for obtaining (meth)acrylic acid with higher purity without causing leakage of a crude solution by preventing complete clogging in a crystallization tube from occurring. The device for crystallizing (meth)acrylic acid includes a crude (meth)acrylic acid solution supply part, a crystallization tube, a heat medium supply tube, a heat medium discharge tube, a storage part of a crude (meth)acrylic acid solution passed through the crystallization tube, a tube for circulating and supplying the crude (meth)acrylic acid solution to the supply part from the storage part, and a pump for circulating and supplying the crude (meth)acrylic acid solution to the supply part from the storage part, and also includes a pressure meter in the circulate-supply tube. The device is used for carrying out dynamic crystallization in a batch manner by circulating the crude (meth)acrylic acid solution to flow the crude solution downward along the inner wall of the crystallization tube in a coating film-like state.

4 Claims, 1 Drawing Sheet

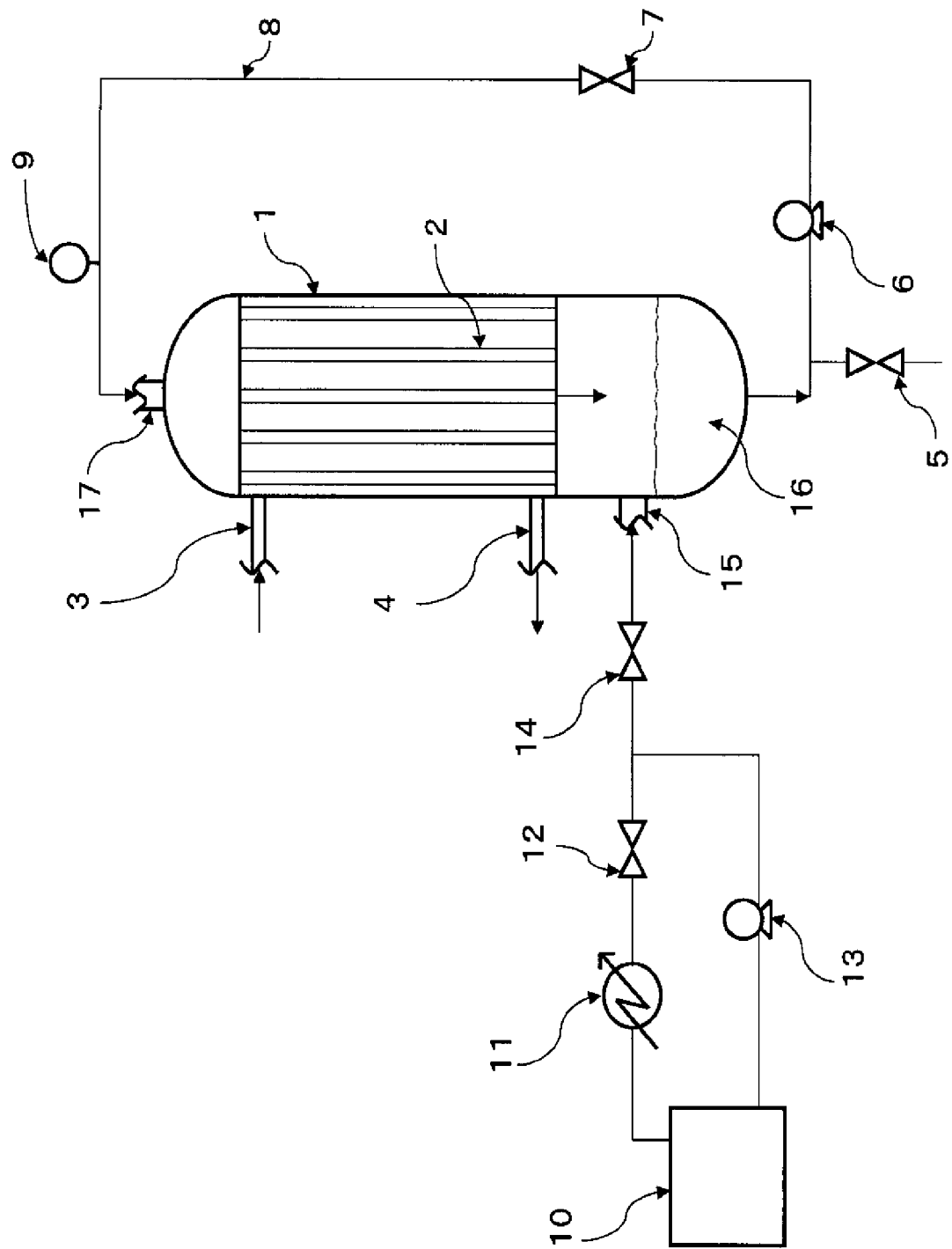

DEVICE AND PROCESS FOR CRYSTALLIZING (METH)ACRYLIC ACID

TECHNICAL FIELD

The present invention relates to a device for crystallizing (meth)acrylic acid to be purified and a process for crystallizing (meth)acrylic acid.

BACKGROUND ART

In general, (meth)acrylic acid is produced by the following steps of:
  obtaining a gas containing (meth)acrylic acid by gas-phase oxidation reaction;
  supplying the gas to a condensing tower or a collecting tower to obtain a crude (meth)acrylic acid solution; and
  purifying (meth)acrylic acid from the crude solution.

As a purification process for (meth)acrylic acid, crystallization is used as well as distillation, diffusion, extraction and the like.

Crystallization may be carried out by merely cooling a crude (meth)acrylic acid solution; however, in industrial mass production, dynamic crystallization is mainly employed. In dynamic crystallization, a crude (meth)acrylic acid solution to be cooled is flowed downward in a coating film-like state along a heat transfer surface of which the reverse side is brought into contact with a cooling medium.

There are various crystallization devices for carrying out such dynamic crystallization. For example, some crystallization devices have crystallization tubes. In such a crystallization device, a heat medium flows outside of the crystallization tubes and a crude (meth)acrylic acid solution is circulated to be repeatedly supplied to the crystallization tubes. Such a crystallization device is generally equipped with a large number of crystallization tubes. The crystallization tube has a thin diameter, and therefore the surface area of the heat transfer surface is enlarged. As a result, the heat energy of a heat medium can be effectively transferred to a crude (meth)acrylic acid solution.

However, it is not easy to evenly grow a crystal on the heat transfer surface of thin and long crystallization tube. In particular, a crystal is unevenly deposited in the lower part of a crystallization tube and finally, may completely clog the crystallization tube in some cases. When a crystallization tube is completely clogged, a crude (meth)acrylic acid solution remains in the upper part above the clogged point. A (meth)acrylic acid crystal is obtained as a melted liquid through sweating step and melting step. In the steps, the remaining crude (meth)acrylic acid solution is mixed to cause a problem that the purity of (meth)acrylic acid is lowered. Further, when pressure significantly increases in the system due to clogging, (meth)acrylic acid may possibly leak out of a crystallization device.

Patent Document 1 discloses a technology for producing (meth)acrylic acid. The technology contains the steps of recovering the heat of a gas obtained by gas-phase oxidation reaction using a heat exchanger, and supplying the gas to a collecting tower in order to obtain a crude (meth)acrylic acid solution. In the technology, when the pressure in a reactor is increased due to clogging of the heat exchanger, the gas is supplied to the collecting tower through a bypass without passing the gas through the heat exchanger. However, the problem of a pressure increase in a reactor and the problem of clogging in a crystallization device are completely different from each other, and there still remains a problem that clogging in a heat exchanger cannot be suppressed by the technology.

PRIOR ART

Patent Document

Patent Document 1: JP-A-2005-336142

SUMMARY OF THE INVENTION

Problems to be Solved by the Invention

As described above, in (meth)acrylic acid production, there is conventionally a technology of keeping the flow rate of a raw material gas which is supplied into a reactor to be constant even if a heat exchanger for recovering heat from a gas obtained by gas-phase oxidation reaction is clogged. Nevertheless, there has been so far no technology for solve the problem of clogging in a crystallization tube. The reason for the fact is thought to be probably that there are a large number of crystallization tubes in a crystallization device and crystallization can be carried out even if some of crystallization tubes are clogged. However, since a crude (meth)acrylic acid solution remains in a completely clogged crystallization tube, there occurs a problem that the purity of the obtained (meth)acrylic acid is lowered. Further, (meth)acrylic acid may possibly leak out of a crystallization device in some cases.

Under the above-mentioned situation, the objective of the present invention is to provide a crystallization device and a crystallization process for obtaining (meth)acrylic acid with higher purity without causing leakage of a crude solution by preventing complete clogging in a crystallization tube from occurring.

Means for Solving the Problems

The inventors of the invention conducted various investigations to solve the above-described problem. As a result, the inventors found that crystallization in the upper part of a crystallization tube can be promoted and particularly, complete clogging in the lower part can be prevented from occurring by setting up a pressure meter in a tube for circulating a crude (meth)acrylic acid solution to a supply part from a storage part in a crystallization device and by decreasing the circulation flow rate when the pressure measured by the pressure meter exceeds a standard value, to complete the present invention.

The device for crystallizing (meth)acrylic acid according to the present invention is characterized in comprising a crude (meth)acrylic acid solution supply part, a crystallization tube, a heat medium supply tube, a heat medium discharge tube, a storage part of a crude (meth)acrylic acid solution passed through the crystallization tube, a tube for circulating and supplying the crude (meth)acrylic acid solution to the supply part from the storage part, and a pump for circulating and supplying the crude (meth)acrylic acid solution to the supply part from the storage part; and further comprising a pressure meter in the circulate-supply tube; wherein the device is used for carrying out dynamic crystallization in a batch manner by circulating the crude (meth)acrylic acid solution to flow the crude solution downward along the inner wall of the crystallization tube in a coating film-like state.

The process for crystallizing (meth)acrylic acid according to the present invention is characterized in that the device for crystallizing (meth)acrylic acid according to the present invention is used; and characterized in comprising the step of decreasing a circulation flow rate of the crude (meth)acrylic acid solution when the pressure value measured by the pressure meter exceeds a predetermined value.

BRIEF DESCRIPTION OF DRAWINGS

FIG. 1 is a schematic diagram showing a crystallization system containing the crystallization device of the present invention for carrying out the crystallization process of the present invention. In the FIG. 1, "1" represents a crystallization device, "2" represents a crystallization tube, "3" represents a heat medium supply part, "4" represents a heat medium discharge part, "5" represents a valve, "6" represents a pump, "7" represents a valve, "8" represents a circulate-supply tube, "9" represents a pressure meter, "10" represents a crude (meth)acrylic acid solution tank, "11" represents a heat exchanger, "12" represents a valve, "13" represents a pump, "14" represents a valve, "15" represents a crude (meth)acrylic acid solution supply part, "16" represents a storage part, and "17" represents a (meth)acrylic acid solution circulate-supply part.

DETAILED DESCRIPTION OF THE INVENTION

First, the crystallization device of the present invention is described.

The crystallization device of the present invention is a batch type one for carrying out dynamic crystallization. Specifically, the prescribed amount of a crude (meth)acrylic acid solution is supplied to the crystallization device, and is flowed downward in a coating film-like state along the inner wall of a crystallization tube with circulation. More specifically, a batch type crystallization device disclosed in JP-A-2005-15478, and a layer crystallization device manufactured by Sulzer Chemtech (Swiss) and the like may be employed.

A crystallization tube is made of a material such as stainless steel and copper excellent in corrosion resistance to (meth)acrylic acid or the like and heat conductivity. A crystallization tube is devised to efficiently transfer cold energy or heat energy of a heat medium to crude (meth)acrylic acid through a heat transfer surface. In general, a crystallization tube is relatively thin and long with a diameter of not less than about 50 mm and not more than about 100 mm and a length of not less than about 5 m and not more than 25 m, and has a large surface area.

The number of crystallization tubes is dependant on the scale of a crystallization device and production scale, and is preferably not less than about 1000 and not more than 2000 in industrial mass production.

In the crystallization device, a supply part of a crude (meth)acrylic acid solution is preferably configured to supply the crude solution to crystallization tubes as evenly as possible.

A supply pipe and a discharge pipe for a heat medium are installed in the crystallization device. A heat medium is supplied to the outer wall parts of the crystallization tubes to transfer cold energy or heat energy of the heat medium to the crude (meth)acrylic acid solution flowing along the inner walls of the crystallization tubes.

A storage part is formed in the crystallization device. Once a crude (meth)acrylic acid solution passed through crystallization tube from a supply part is stored in the storage part, and then the crude solution is extracted out of the storage part using a circulate-supply tube, and again supplied to the supply part for circulation. A pump for circulating and supplying a crude (meth)acrylic acid solution to a supply part is preferably installed at the lowest position of a circulate-supply tube.

The crystallization device of the present invention is equipped with a pressure meter in the circulate-supply tube. Such a pressure meter is exemplified by a bourdon tube pressure meter, a bellows type pressure meter, and a diaphragm type pressure meter. Among the examples, a diaphragm type pressure meter is preferred.

The installation position of a pressure meter may be properly adjusted and if possible, it is preferable to set up the pressure meter at the highest position of a circulate-supply tube or a position from the highest position to the crystallization device so as to reflect the pressure in a crude (meth)acrylic acid solution supply part of the crystallization device.

The crystallization device of the present invention preferably further comprises a means for controlling an amount of the crude (meth)acrylic acid solution to be circulated and supplied on the basis of the pressure value measured by the pressure meter. The crystallization process of (meth)acrylic acid according to the present invention described later can be readily practiced by using such a crystallization device. Such a means is exemplified by a valve capable controlling a passing solution amount and a pump capable controlling a discharge amount.

Next, the process for crystallizing (meth)acrylic acid according to the present invention is described with reference to FIG. 1.

A crude (meth)acrylic acid solution as a raw material for crystallization is not particularly limited as long as it contains impurity in addition to (meth)acrylic acid as the objective compound. Such a crude solution is exemplified by a crude (meth)acrylic acid solution obtained by carrying out gas-phase oxidation reaction to obtain a (meth)acrylic acid-containing gas, and contacting the obtained gas with a collecting liquid or condensing the obtained gas. The crude solution is also exemplified by a crude (meth)acrylic acid solution obtained by removing impurity with low boiling point from the above-described crude solution.

In order to obtain (meth)acrylic acid with higher purity, purification by crystallization may be repeated two or more times. Specifically, once (meth)acrylic acid is crystallized to be purified, the purified (meth)acrylic acid is melted, and the melted liquid is supplied to a crystallizer instead of a crude (meth)acrylic acid solution to repeat crystallization.

The temperature of a crude (meth)acrylic acid solution obtained through gas-phase oxidation reaction is high; and in the present invention, (meth)acrylic acid is purified by crystallization in a batch manner but not a continuous manner. Therefore, it is preferred that a crude (meth)acrylic acid solution is temporarily stored in the tank 10.

When crystallization is carried out but the temperature of a crude (meth)acrylic acid solution is high, it is preferred to recover and use the heat by the heat exchanger 11. Whether the heat is recovered or not before the crude (meth)acrylic acid solution is supplied to the crystallization device 1 can be easily determined by the valve 12 and the valve 14.

The amount of a crude (meth)acrylic acid solution to be supplied to the crystallization device 1 may be determined in accordance with the scale of the crystallization device 1 and others. A crude (meth)acrylic acid solution is generally supplied to the storage part 16 from the crude (meth)acrylic acid solution supply part 15 of the crystallization device 1.

Next, in order to start crystallization, the supplied crude (meth)acrylic acid solution is circulated and supplied to the (meth)acrylic acid solution circulate-supply part 17 of the crystallization device 1 through the circulate-supply tube 8 by using the pump 6 in a state where the valve 5 is closed and the valve 7 is opened.

In crystallization, a cooling medium is circulated to cool the crude (meth)acrylic acid solution which is circulated and supplied to the crystallization device 1 through the circulate-supply tube 8, thereby crystallizing (meth)acrylic acid on the inner surface of the crystallization tube 2. At that time, the inner pressure of the tube is constantly monitored by the pressure meter 9 installed on the circulate-supply tube 8, and the amount of the crude (meth)acrylic acid solution to be circulated is adjusted in accordance with the measured pressure value in order to keep the pressure in the circulate-supply tube 8 within a prescribed range.

A proper circulation flow rate of a crude (meth)acrylic acid solution is different depending on the scale of the crystallization device or the like, and therefore may be properly adjusted. In general, the circulation flow rate is adjusted such that the pressure value measured by the pressure meter 9 installed in the circulate-supply tube is 0.01 MPa or higher. When the pressure value is 0.01 MPa or higher, excellent crystallization is made possible without decreasing crystallization efficiency to an excess extent. On the other hand, the upper limit thereof is not particularly limited; however, it is generally preferable to adjust the circulation flow rate such that the pressure value in the circulate-supply tube is 0.5 MPa or lower. In the present invention, the pressure of the circulate-supply tube means a pressure excluding the atmospheric pressure, that is, gauge pressure.

As described above, it is not easy to evenly grow a crystal on a heat transfer surface of a crystallization tube, and a crystal tends to be unevenly deposited particularly in the lower part of the crystallization tube 2. When a crystal is unevenly deposited and thereby, a crude (meth)acrylic acid solution becomes difficult to be flowed, the pressure value measured by the pressure meter 9 installed in the circulate-supply tube 8 becomes high. In the present invention, when the measured pressure value exceeds a predetermined value, the circulation flow rate of a crude (meth)acrylic acid solution is decreased so that crystallization in the upper part of the crystallization tube 2 is promoted and at the same time, crystallization in the lower part is controlled to suppress the complete clogging of the crystallization tube. As a result, crystallization becomes easy to be evenly promoted in a crystallization tube and the remaining of a crude (meth)acrylic acid solution in the crystallization tube is eliminated, and thus a crystal with higher purity can be obtained.

More specifically, in the crystallization process of the present invention, the circulation flow rate of a crude (meth)acrylic acid solution is adjusted so that the difference between the maximum value and the minimum value of the measured pressure becomes within 100% of the minimum value, more preferably within 50% of the minimum value. If the fluctuation of the pressure in the circulate-supply tube is in the range, (meth)acrylic acid can be purified by crystallization more reliably and stably, and the purity of the obtained (meth)acrylic acid can be further improved. The minimum value of the measured pressure in the present invention means a pressure value measured at the time point when the circulating and supplying amount reaches a set value for the first time after starting the circulation and supply of the crude (meth)acrylic acid solution. When the circulation and supply is continued after the circulating and supplying amount of the crude (meth)acrylic acid solution reaches the set value, the pressure is gradually increased as crystallization of (meth)acrylic acid in the crystallization tube is promoted. Therefore, in the above embodiment, when the measured pressure value seems to exceed the minimum value, that is, 100% of the initial value, or preferably 50% of the initial value, the circulation flow rate of a crude (meth)acrylic acid solution is decreased to adjust the measured pressure value within the above-mentioned range.

A means for adjusting the pressure in the circulate-supply tube can be properly selected. For example, it is possible to employ, as the valve 7 of the circulate-supply tube, a valve which can adjust an opening and closing degree in a step-by-step manner or continuously to control an amount of a passing solution but not a valve which can merely be opened or closed to stop the circulation and supply of a solution or pass the solution in an amount corresponding to the discharge amount of the pump. Further, as the pump 6 for circulation and supply, a pump by which a discharge amount can be controlled may be employed. In the present invention process, when the measured pressure value in the circulate-supply tube exceeds the defined range, for example, the opening degree of the valve is lowered or the discharge amount of the pump is decreased by the above-described adjustment means to control the pressure in the defined range. On the other hand, when the measured pressure value is less than the defined range, for example, the opening degree of the valve or the discharge amount of the pump may be increased.

Next, in order to improve the purity of a (meth)acrylic acid crystal, it is preferable that the heat medium to be supplied to the crystallization device 1 is changed to a heating medium from a cooling medium to carry out sweating step. In sweating step, the surface of a (meth)acrylic acid crystal in the crystallization tube 2 is partially melted.

In the crystallization step, the amount of impurity existing in a solution is relatively increased as crystallization of (meth)acrylic acid progresses. As a result, the impurity is sometimes deposited on the surface of a (meth)acrylic acid crystal. Therefore, the purity of the crystal can be increased by partially melting the surface of the (meth)acrylic acid crystal and discharging the melted part. Such a partial melting treatment is called as sweating operation.

A mother solution of the above-mentioned crystallization step is stored in the storage part 16 in the lower part of the crystallization device 1. Further, the partially melted liquid obtained in the sweating step is also to be stored in the storage part 16. The mother solution and partially melted liquid are transported through the valve 5.

Next, the melting step of a crystal is carried out. Specifically, a heat medium is changed to a heating medium having relatively high temperature to melt a crystal in a crystallization tube, and the melted liquid obtained from the crystallization tube 2 is circulated and supplied to a (meth)acrylic acid solution circulate-supply part 17 of the crystallization device 1 through the circulate-supply tube 8 so that the melted liquid is flowed downward on a (meth)acrylic acid crystal in the inside of the crystallization tube 2 to promote melting.

In the melting step, a polymerization inhibitor or a concentrated solution thereof may be charged into the storage part 16 of the crystallization device 1. The obtained melted liquid of (meth)acrylic acid has high concentration and in addition, is heated in the melting step; therefore, impurity such as a dimmer may possibly be produced. However, such impurity can be suppressed by using a polymerization inhibitor.

A polymerization inhibitor is not particularly limited, and is exemplified by a N-oxyl compound such as 2,2,6,6-tetramethylpyperidino-1-oxyl; a phenol compound such as p-methoxyphenol; a manganese salt compound such as manganese acetate; a dialkyldithiocarbamate salt compound such as copper dibutyldithiocarbamate; a nitroso compound; an amine compound; and a phenothiazine compound. In the case that one or more kinds of the polymerization inhibitors selected from the group consisting of the above-described N-oxyl compound, phenol compound and manganese salt compound are used, it is made possible to obtain (meth)acrylic acid which has sufficiently high quality and is more excellent in color tone. Only one kind of a polymerization inhibitor may be singly used, or two or more kinds of polymerization inhibitors may be used in combination.

As a solvent usable when a concentrated solution of a polymerization inhibitor is used, (meth)acrylic acid, water, acetic acid and the like may be used, and (meth)acrylic acid is preferably used.

In order to further improve the purity, the obtained melted liquid of (meth)acrylic acid may be further repeatedly subjected to the crystallization step, sweating step and melting step. In order to obtain (meth)acrylic acid with high purity, such purification by crystallization is repeated generally three times or more and 5 times or less.

The obtained melted liquid of (meth)acrylic acid with high purity is transported through the valve 5.

When (meth)acrylic acid is purified by crystallization in a batch manner, conventionally, the prescribed amount of a crude (meth)acrylic acid solution is supplied into a crystallization device and the crude solution is merely circulated and supplied without specific control. Specifically, there has not been any means for detecting the uneven existence of a crystal from the upper part to the lower part of a crystallization tube, the clogging of a crystallization tube or the like. It has not been also done to prevent the above situation. Accordingly, the purity of the obtained (meth)acrylic acid is lowered in the case of crystallization purification over a long period and it has been impossible to obtain a product with stable quality. In addition, when pressure significantly increases in a system due to clogging, an adverse effect on productivity is occurred. For example, a crude solution is leaked and the crystallization operation needs to be temporarily stopped.

In contrast, according to the crystallization process of the present invention using the crystallization device of the invention, as compared with a conventional technologies, it is made possible to produce highly pure (meth)acrylic acid with suppressed contamination with a crude (meth)acrylic acid solution without causing leakage of a crude solution. Further, it is also made possible to decrease the number of times of crystallization for obtaining (meth)acrylic acid with prescribed purity and thus, efficient production is made possible.

EXAMPLES

Hereinafter, the present invention is described in detail with Examples. However, the present invention is not limited to the Examples in any way, and it is possible to carry out the present invention according to the Examples with an additional appropriate change within the range of the specification. Such a change is also included in the technical scope of the present invention.

Example 1

(1) Production of Crude Acrylic Acid Solution

Propylene was subjected to gas-phase oxidation reaction in a reactor. The obtained reaction gas was supplied into a collecting tower, and was contacted with a collecting liquid to obtain a crude acrylic acid solution from the bottom of the collecting tower. The obtained crude acrylic acid solution was analyzed to find that the solution contained 90.0% by mass of acrylic acid, 3.2% by mass of water, 1.9% by mass of acetic acid, 0.6% by mass of maleic acid, 1.5% by mass of acrylic acid dimer, 0.07% by mass of furfural, 0.27% by mass of benzaldehyde, 0.06% by mass of formaldehyde, 0.1% by mass of hydroquinone, and 2.3% by mass of other impurities. The bottom temperature of the collecting tower at that time, which corresponds to the temperature of the crude acrylic acid solution immediately after taken out of the collecting tower, was 91° C. Acrylic acid was crystallized to be purified from the obtained crude acrylic acid solution using a crystallization system schematically shown in FIG. 1. The scale of the used crystallization system was in an experimental scale, and the number of crystallization tubes in a crystallization device was three.

After the temperature of the crude acrylic acid solution was adjusted by the heat exchanger 11 in the range of ±5° C. of the temperature at the time when crystallization was started, the crude acrylic acid solution was supplied to the storage part of the crystallization device 1. Specifically, in the crystallization device 1, the crude acrylic acid solution could be circulated and supplied to the circulate-supply part 17 from the storage part 16 through the circulate-supply tube 8 by the circulation pump 6. Each crystallization tube 2 was a metal tube with a length of 6 m and an inner diameter of 70 mm. The crude acrylic acid solution supplied to the upper part was allowed to flow downward in a coating film-like state along the inner wall of the crystallization tube 2. The surface of the crystallization tube 2 was constituted with a double jacket, and the temperature was controlled by a heat medium supplied from the heat medium supply part 3 and discharged out of the heat medium discharge part 4. The crude acrylic acid passed through the crystallization tube 2 was temporarily stored in the storage part and then continuously circulated and supplied to the circulate-supply part 17.

(2) Crystallization Step

After supply of a cooling medium to the above-described crystallization device 1 was started, the circulation and supply of the crude acrylic acid solution was started. The amount of a crystal deposited on the inner wall of the crystallization tube 2 was estimated from the amount of the crude acrylic acid solution in the storage part 16. The circulation was continued until about 60 to 90% by mass of acrylic acid contained in the crude acrylic acid solution as a raw material was crystallized.

At that time, the inner pressure of the tube was constantly monitored by the pressure meter 9 installed at a highest position in the circulate-supply tube 8. The circulating and supplying amount of the crude acrylic acid solution was adjusted and the pressure of the circulate-supply tube 8 was kept within the range of not less than 0.10 MPa and not more than 0.14 MPa by changing the opening degree of the valve 7 capable of controlling the amount of the passing solution within the range of between 30 to 40%. In this case, the difference between the maximum value and the minimum value of the measured pressure was 0.04 MPa, which was within 50% of the minimum value.

(3) Sweating Step

Next, the circulation pump 6 was stopped and the temperature of a heat medium was increased near the freezing point of the crude acrylic acid solution to melt about 2 to 5% by mass of the crystal for sweating. The amount of melted part was estimated based on the increase of the crude acrylic acid solution in the storage part 16. Thereafter, the valve 5 was opened to transfer the mother liquid in the crystallization step and the partially melted liquid to a mother solution tank.

(4) Melting Step

The temperature of a heat medium was increased up to 37° C. to melt the crystal on the inner wall surface of the crystallization tube. The melted liquid was circulated and supplied to the circulate-supply part 17 of the crystallization device 1 and allowed to flow downward on the acrylic acid crystal in the inside of the crystallization tube 2. After the crystal was completely melted, the pump 6 was stopped and the valve 7 was closed to storage the melted liquid of acrylic acid in the storage part 16 of the crystallization device 1.

(5) Repeat of Steps from Crystallization to Melting

The crystallization step to the melting step of the above-described (2) to (4) were repeated to carry out crystallization purification for 4 times in total.

In the melting step at the third time and fourth time, an acrylic acid solution containing 5% by mass of p-methoxyphenol as a polymerization inhibitor was fed to the storage part 16 of the crystallization device 1.

The obtained acrylic acid to be purified was analyzed; as a result, it was found that the acrylic acid had a purity of 99.94% by mass, and additionally contained 92 ppm by mass of water, 440 ppm by mass of acetic acid, 2 ppm by mass of maleic acid, 45 ppm by mass of acrylic acid dimer, 0.2 ppm by mass of furfural and 0.1 ppm by mass of benzaldehyde, and no formaldehyde was detected. The production efficiency through the above steps was 10.02 kg/h.

Example 2

Acrylic acid was produced in the same manner as Example 1, except that the pressure of the circulate-supply tube 8 was kept within the range of not less than 0.10 MPa and not more than 0.16 MPa in the crystallization step. In this case, the difference between the maximum value and the minimum value of the measured pressure was 0.06 MPa, which was within 100% of the minimum value.

The obtained acrylic acid to be purified was analyzed; as a result, it was found that the acrylic acid had a purity of 99.89% by mass, and additionally contained 153 ppm by mass of water, 710 ppm by mass of acetic acid, 4 ppm by mass of maleic acid, 100 ppm by mass of acrylic acid dimer, 0.5 ppm by mass of furfural and 0.4 ppm by mass of benzaldehyde, and no formaldehyde was detected. The production efficiency through the above steps was 9.98 kg/h.

Comparative Example 1

Acrylic acid was produced in the same manner as Example 1, except that the opening degree of the valve 7 was fixed at 40% and the pressure was not adjusted based on the pressure value measured by the pressure meter 9 installed in the circulate-supply tube 8 in the crystallization step. At that time, the measured pressure value was increased up to 0.21 MPa. In this case, the difference between the maximum value and the minimum value of the measured pressure was 0.11 MPa, which exceeded 0.10 MPa that was 100% of the minimum value.

The obtained acrylic acid to be purified was analyzed; as a result, it was found that the acrylic acid had a purity of 99.86% by mass, and additionally contained 171 ppm by mass of water, 860 ppm by mass of acetic acid, 5 ppm by mass of maleic acid, 120 ppm by mass of acrylic acid dimer, 0.7 ppm by mass of furfural and 0.6 ppm by mass of benzaldehyde, and no formaldehyde was detected. The production efficiency through the above steps was 9.98 kg/h. In addition, under the above-mentioned condition, there occurred a problem such that leakage of a crude acrylic acid solution was observed from the crystallization device during the crystallization purification.

As described above, in crystallization step, it was made clear that when the amount of a (meth)acrylic acid solution to be circulated and supplied was not adjusted on the basis of the pressure of a circulate-supply tube of a crystallization device, the purity of the obtained (meth)acrylic acid was lowered and leakage of the crude (meth)acrylic acid solution out of the crystallization device occurred.

On the other hand, when the circulate-supply amount was adjusted on the basis of the said pressure and the pressure was maintained in a predetermined range, the purity of the obtained (meth)acrylic acid became high. In addition, when the pressure was kept in a more preferable range, that is, in the case of Example 1, the purity of the obtained (meth)acrylic acid became higher.

As the above-described result, it was proved that the present invention can provide (meth)acrylic acid with higher purity.

Industrial Applicability

In general, since a crude (meth)acrylic acid solution is gradually cooled in a crystallization tube of a crystallization device, a crystal tends to be unevenly deposited in the lower part of the crystallization tube and it is thus not easy to evenly grow the crystal on a heat transfer surface. If such a state is left, the crystallization tube is finally completely clogged. However, crystallization step can be continued, since a large number of crystallization tubes are installed in a crystallization device and all of the crystallization tubes are not completely clogged. In addition, a crystallization tube clogged in crystallization step is again opened in sweating step and melting step. Therefore, such a clogging has not been particularly regarded as a problem. However, since a crude (meth)acrylic acid solution remains in the completely clogged crystallization tube, the purity of the obtained (meth)acrylic acid is lowered. As a result, there occurs a problem such that the number of times for crystallization has to be increased to obtain the prescribed purity of (meth)acrylic acid, thereby resulting in a decrease in production efficiency.

On the other hand, according to the present invention, the complete clogging of a crystallization tube can be previously prevented by adjusting the circulation flow rate of a crude (meth)acrylic acid solution in a circulate-supply tube of a crystallization device in accordance with the pressure of the solution, and thus it is made possible to obtain (meth)acrylic acid with higher purity without causing leakage of the crude solution. Consequently, the present invention is industrially remarkably advantageous to efficiently produce (meth) acrylic acid with high quality.

The invention claimed is:

1. A process for crystallizing (meth)acrylic acid using a device for crystallizing (meth)acrylic acid, wherein the device for crystallizing (meth)acrylic acid includes:

a crude (meth)acrylic acid solution supply part, a crystallization tube, a heat medium supply tube, a heat medium discharge tube, a storage part of a crude (meth)acrylic acid solution passed through the crystallization tube, a tube for circulating and supplying the crude (meth) acrylic acid solution to the supply part from the storage part, and a pump for circulating and supplying the crude (meth)acrylic acid solution to the supply part from the storage part; and a pressure meter in the circulate-supply tube, the device being used for carrying out dynamic crystallization in a batch manner by circulating the crude (meth) acrylic acid solution to flow the crude solution downward along the inner wall of the crystallization tube in a coating film-like state, said process for crystallizing (meth)acrylic acid comprising:

decreasing a circulation flow rate of the crude (meth) acrylic acid solution to the supply part from the storage part when the pressure value measured by the pressure meter exceeds a predetermined value.

2. The crystallization process according to claim 1, wherein the circulation flow rate of the crude (meth)acrylic acid solution is controlled to adjust the difference between the maximum value and the minimum value of the measured pressure to be within 100% of the minimum value.

3. A process for crystallizing (meth)acrylic acid using a device for crystallizing (meth)acrylic acid,
wherein the device for crystallizing (meth)acrylic acid includes:
a crude (meth)acrylic acid solution supply part, a crystallization tube, a heat medium supply tube, a heat medium discharge tube, a storage part of a crude (meth)acrylic acid solution passed through the crystallization tube, a tube for circulating and supplying the crude (meth) acrylic acid solution to the supply part from the storage part, and a pump for circulating and supplying the crude (meth)acrylic acid solution to the supply part from the storage part;
a pressure meter in the circulate-supply tube; and
a means for controlling an amount of the crude (meth) acrylic acid solution to be circulated and supplied on the basis of the pressure value measured by the pressure meter,
the device being used for carrying out dynamic crystallization in a batch manner by circulating the crude (meth) acrylic acid solution to flow the crude solution downward along the inner wall of the crystallization tube in a coating film-like state,
said process for crystallizing (meth)acrylic acid comprising:
decreasing a circulation flow rate of the crude (meth) acrylic acid solution to the supply part from the storage part when the pressure value measured by the pressure meter exceeds a predetermined value.

4. The crystallization process according to claim 3, wherein the circulation flow rate of the crude (meth)acrylic acid solution is controlled to adjust the difference between the maximum value and the minimum value of the measured pressure to be within 100% of the minimum value.

* * * * *